United States Patent [19]

Ishiguro et al.

[11] Patent Number: 5,534,546

[45] Date of Patent: Jul. 9, 1996

[54] INDENE DERIVATIVES AND ANTIMICROBIAL AGENTS CONTAINING SAME

[75] Inventors: Yukio Ishiguro, Tochigi; Youji Sonoda, 3490-90 Nagara, Gifu-shi gifu; Kenji Okamoto, Tochigi; Takamitsu Okamoto, Tochigi; Hideki Sakamoto, Tochigi, all of Japan

[73] Assignees: Kagome Kabushiki Kaisha; Youji Sonoda, Japan

[21] Appl. No.: 372,729

[22] Filed: Jan. 17, 1995

Related U.S. Application Data

[63] Continuation of Ser. No. 218,537, Mar. 28, 1994, abandoned.

[30] Foreign Application Priority Data

Mar. 31, 1993 [JP] Japan ................. 5-098669
Apr. 12, 1993 [JP] Japan ................. 5-109984

[51] Int. Cl.$^6$ .................................. A61K 31/12
[52] U.S. Cl. ........................... 514/681; 568/327
[58] Field of Search ................. 568/327; 514/681

[56] References Cited

U.S. PATENT DOCUMENTS 4,069,326  1/1978  Teulon ..................... 568/327
4,333,949  6/1982  Sturm et al. .............. 514/651
5,329,050  6/1994  Weisse et al. ............. 568/327

*Primary Examiner*—James H. Reamer
*Attorney, Agent, or Firm*—Majestic, Parsons, Siebert & Huse

[57] ABSTRACT

New indene derivative, obtainable from etiolated seedlings of Adlay and shown by Formulas (1) and (2) given below, have antimicrobial effects and can serve as effective components of antimicrobial agents:

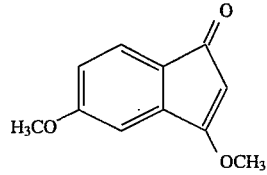

FIG. (1)

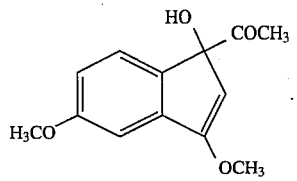

Formula (2)

4 Claims, No Drawings

INDENE DERIVATIVES AND ANTIMICROBIAL AGENTS CONTAINING SAME

This is a continuation of application Ser. No. 08/218,537, filed Mar. 28, 1994, now abandoned.

BACKGROUND OF THE INVENTION

This invention relates to indene derivatives and antimicrobial agents containing such indene derivatives as effective components.

It has been known that etiolated seedlings of Adlay have antimicrobial activities, whether in a dried form, as a squeezed juice or as an extract. As examples of compound having this kind of antimicrobial activity, Japanese Patent Publications Tokkai 2-270825 and 3-240473 have suggested monoglycerides of stearic acid and palmitic acid, as well as their derivatives.

SUMMARY OF THE INVENTION

It is an object of the present invention to provide new indene derivatives which are isolated from etiolated seedlings of Adlay and show superior antimicrobial activities.

The present inventors have discovered, as a result of their diligent investigations into the antimicrobial activities exhibited by etiolated seedlings of Adlay in a dried form, as a squeezed juice or an extract, that new indene derivatives can be isolated if etiolated seedlings of Adlay are processed in a certain specified manner.

DETAILED DESCRIPTION OF THE INVENTION

This invention relates to new indene derivatives shown by Formulas (1) and (2) shown below, as well as antimicrobial agents containing such indene derivatives as their effective component:

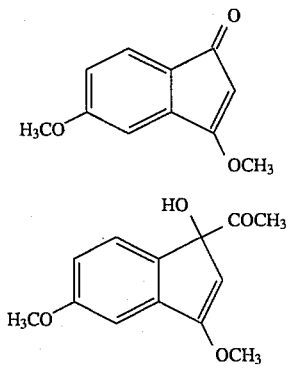

FIG. (1)

Formula (2)

A process for obtaining the indene derivatives as shown by Formulas (1) and (2) is described next. First, etiolated seedlings of Adlay are obtained by causing Adlay seeds to germinate in a dark environment, as will be described in detail below by way of examples. Examples of Adlay which may be used according to the present invention include local varieties such as Tokuda, Nakazato, Okayama and Kuroishi. The invention is not limited by the use of any particular kind. As for the process itself, use may be made of any usual method of obtaining etiolated seedlings by germinating in the dark. For example, Adlay seeds may be germinated in the dark for 4–8 days at 25° C. Nearly the entirety of etiolated seedlings of Adlay thus obtained can be used for the purpose of this invention.

Next, the etiolated seedlings of Adlay thus obtained, or what may be obtained therefrom by grinding, freeze-drying or pulverizing, are subjected to an extraction process by using methyl alcohol or ethyl alcohol such that an extract is obtained. Next, the extract thus obtained is subjected to a liquid-liquid partition extraction process by using a combination of methyl alcohol or ethyl alcohol and chloroform. After a chloroform layer is separated, another liquid-liquid partition process is carried out by using a combination of this chloroform and acetone. A simple lipid, which is easily dissolved in acetone, is obtained therefrom after an acetone layer is separated.

Lastly, this simple lipid is subjected to a chromatographical separation process by chromatography using mobile phases with different polarities. Separation processes are repeated and the two kinds of target compounds are separated by their different retention times. It is preferable to carry out the chromatographical separation process by a combination of gel permeation chromatography and high performance liquid chromatography by using mobile phases with different polarities.

The physical and chemical properties of one of the two compounds thus separated are as follows:

(1) Molecular weight: 190 ($C_{11}H_{10}O_3$)

(2) Infrared spectrum: 1585, 1703, 3050cm$^{-1}$ (3) Chemical shift by $^1$H-NMR: 3.99 (3H, s), 4.09 (3H, s), 5.98 (1H, s), 7.19 (1H, dd, J=8.79, 2.56), 7.56 (1H, d, J=2.56), 8.00 (1H, d, J=8.79)

(4) Chemical shift by $^{13}$C-NMR: 57.7, 58.7, 105.6, 112.3, 118.1, 126.1, 133.2, 136.6, 167.2, 169.3, 181.5 From these physical and chemical properties, the first of the separated compounds has been determined to be the indene derivative shown by Formula (1) which is 3,5-dimethoxy-1H-inden-1-one.

The physical and chemical properties of the other of these two separated compounds are as follows:

(1) Molecular weight: 234 ($C_{13}H_{14}O_4$)

(2) Infrared spectrum: 1569, 1712, 3401cm$^{-1}$ (3) Chemical shift by $^1$H-NMR: 2.01 (3H, s), 3.84 (3H, s), 4.00 (3H, s), 5.68 (1H, s), 7.08 (1H, dd, J=8.55, 2.67), 7.37 (1H, d, J=2.67), 7.57 (1H, d, J=8.55)

(4) Chemical shift by $^{13}$C-NMR: 31.6, 55.9, 57.1, 76.0, 99.1, 109.5, 117.2, 128.7, 129.0, 137.0, 160.3, 168.3, 205.0

From these physical and chemical properties, the second of the separated compounds has been determined to be the indene derivative shown by Formula (2) which is 1-acetyl-1-hydroxy-3,5-dimethoxy-1H-inden.

As will be described more in detail below, the indene derivative shown by Formula (1) demonstrates superior antimicrobial activities against bacteria, yeasts and fungi, and the indene derivative shown by Formula (2) demonstrates superior antimicrobial activities against bacteria. In other words, both these indene derivatives are useful to foods and cosmetic items as natural antimicrobial agents.

EXAMPLES

Test No. 1: Separation of indene derivative shown by Formula (1)

Etiolated seedlings of Adlay were obtained by geminating Adlay seeds of Tokuda variety for four days at 25° C. After these seedlings were ground, they were freeze-dried at shelf temperature of 20° C. to obtain a freeze-dried object. After methyl alcohol 6 liters was added to 150 g of this freeze-dried object, it was homogenized and left quietly for 48 hours at room temperatures. It was then filtered to obtain an extract solution. Methyl alcohol 6 liters was added to the residue to similarly obtain another extract solution and this extract solution was added to the earlier obtained extract solution. This mixture was heated at 40°–45° C. under a reduced pressure condition to evaporate the methyl alcohol, obtaining 30 g of an extract.

Methyl alcohol 100 ml and chloroform 200 ml were added to 30 g of this extracted object. The mixture was stirred, 60 ml of 0.8% aqueous solution of potassium chloride was added thereto and the mixture was left quietly. After a chloroform layer was removed and the solution was heated at 40°–45° C. under a reduced pressure condition to condense it to 1 ml, 10 ml of acetone and 0.2 ml of 10% methyl alcohol solution of magnesium chloride were added, mixed and stirred. After it was cooled with ice for one hour, a supernatant acetone solution was collected by centrifugal separation. Acetone 10 ml and 10% methyl alcohol solution of magnesium chloride 0.2 ml were added to the residue to similarly obtain another acetone solution, which was added to the earlier obtained acetone solution. The mixed acetone solution was heated at 40°–45° C. under a reduced pressure condition to evaporate acetone and to obtain 7.1 g of a simple lipid which dissolves in acetone easily.

The simple lipid 7.1 g thus obtained was dissolved in chloroform for gel permeation chromatography by using two polystyrene polymer columns (JAIGEL 1H, trade name of Nippon Bunseki Kogyo Co., Ltd.: 8.0 mmϕ×500 mm). Chloroform was used in the mobile phase with flow rate of 3.5 ml/minute. Refractive index (RI) was detected, and four partitions showing principal peaks were obtained. Antimicrobial effects of these partitions were tested by the paper disc method against Bacillus subtilis, Saccharomyces cerevisiae and Aspergillus niger, and 1.8 g of a partition showing the strongest antimicrobial activity with retention time (Rt)=55–64 minutes was obtained.

This partition 1.8 g was dissolved in methyl alcohol for a first high performance liquid chromatographic test by using an ODS column (CAPCELL PAK $C_{18}$, trade name of Shiseido Co., Ltd.: 20 mmϕ×250 mm). The mobile phase was methyl alcohol/water=20/80 (weight ratio) to start with and it was changed by a linear gradient method to 100/0 after 30 minutes. The flow rate was 3.0 ml/minute. Ultraviolet absorbance (at 254 nm) was detected and six partitions showing principal peaks were obtained. By a similar antimicrobial test as described above, a partition of 146.4 mg showing the strongest antimicrobial activity with Rt=34–38 minutes was obtained. This partition of 146.4 mg thus obtained was dissolved in methyl alcohol for a second high performance liquid chromatographic test by using a CAPCELL PAK $C_{18}$ column. The mobile phase for this test was methyl alcohol/water=50/50 (weight ratio) with flow rate of 3.0 ml/minute. Ultraviolet absorbance (at 254 nm) was detected and eight partitions showing principal peaks were obtained. By a similar antimicrobial test as described above, 12.8 g of a compound showing the strongest antimicrobial activity against all test bacteria with Rt=45 minutes was obtained.

The physical and chemical properties of the compound thus obtained are as presented above, and it was 3,5-dimethoxy-1H-inden-1-one shown by Formula (1).

Test No. 2: Separation of indene derivative shown by Formula (2)

An extract was obtained from 150 g of freeze-dried etiolated Adlay as in Test No. 1 by using methyl alcohol, and this extract was subjected to a liquid-liquid partition extraction process with a combination of methyl alcohol and chloroform and then to another liquid-liquid partition extraction process with a combination of chloroform and acetone to obtain a simple lipid which is easily dissolved in acetone. This simple lipid was used as in Test No. 1 for gel permeation chromatography and further for first high performance liquid chromatography to obtain a partition with Rt=34–38 minutes, having the strongest antimicrobial activity.

This partition was dissolved in methyl alcohol for second high performance liquid chromatography by using a CAPCELL PAK $C_{18}$ column. The mobile phase in this case was methyl alcohol/water=50/50 (weight ratio) with flow rate of 3.0 ml/minute. Ultraviolet absorbance (at 254 nm) was detected and eight partitions showing principal peaks were obtained. By a similar antimicrobial test as described above, a partition with Rt=30 minutes and showing antimicrobial effects only against Bacillus subtilis was selected and used for a third high performance liquid chromatography process by again using a CAPCELL PAK $C_{18}$ column. The mobile phase this time was methyl alcohol/water=25/75 (weight ratio) with flow rate of 3.0 ml/minute. Ultraviolet absorbance (at 254 nm) was detected and 1.5 mg of a compound with Rt=23 minutes was isolated.

The physical and chemical properties of the compound thus isolated are as presented above, and it was 1-acetyl-1-hydroxy-3,5-dimethoxy-1H-inden shown by Formula (2).

Test No. 3: Antimicrobial activities of isolated indene derivatives

Antimicrobial activities of the isolated indene derivatives shown by Formula (1) were tested against Bacillus subtilis, Saccharomyces cerevisiae and Aspergillus niger. Antimicrobial activities of the isolated indene derivatives shown by Formula (2) were tested against Bacillus subtilis. Both tests were carried out by a paper disk method. Use, as medium, was made of trypso-soya agar (product by Nissui Pharmaceutical Co., Ltd., containing peptone 1.5% soybean peptone 0.5% NaCl 0.5%, and agar 1.5%) for Bacillus subtilis and potato dextrose agar (product by Nissui Pharmaceutical Co., Ltd., extract of potato 0.4%, glucose 2.0%, agar 1.5%) for Saccharomyces cerevisiae and Aspergillus niger. These agar materials (15 ml) were each poured into a Petri dish to prepare a planar medium.

Bacteria to be tested were inoculated on a similarly prepared 15 ml agar medium and the latter was then place on top of the aforementioned planar medium and solidified. Paper discs (product by Toyo Roshi Kaisha, Ltd. with diameter=8 mm; thin) were placed on such a superposed plane medium, and 20 μl each of the isolated indene derivative shown by Formula (1) and (2) was dropped on the paper discs (200 μg/paper disc). The diameters of the halos were measured after 24 hours of culturing in the case of Bacillus subtilis and 48 hours in the case of Saccharomyces cerevisiae and Aspergillus niger. Averages were taken from values obtained from five paper discs and antimicrobial activities were obtained according to Formula (3) shown below:

*Antimicrobial activity (mm)=(Diameter (mm) of halo)−(Diameter (mm) of paper disc)*

The antimicrobial activity of the indene derivative shown by Formula (1) was 20.0 mm against Bacillus subtilis, 11.5 mm against Saccharomyces cerevisiae and 11.5 mm against Aspergillus niger, indicating that the indene derivative shown by Formula (2) has superior antimicrobial activities against bacteria, yeasts and fungi. The antimicrobial activity of the indene derivative shown by Formula (2) was 24.0 mm against Bacillus subtilis, indicating that the indene derivative shown by Formula (2) has superior antimicrobial activities against bacteria.

In summary, it has been shown that the indene derivatives according to the present invention are useful as natural antimicrobial agent.

What is claimed is:

1. An indene derivative shown by Formula (1) given below:

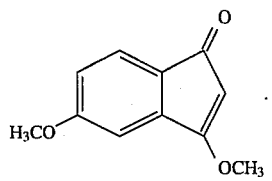

FIG. (1)

2. An indene derivative shown by Formula (2) given below:

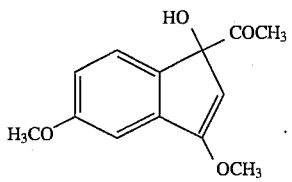

Formula (2)

3. An antimicrobial agent having the indene derivative of claim 1 as effective component.

4. An antimicrobial agent having the indene derivative of claim 2 as effective component.

* * * * *